US007708019B2

(12) United States Patent
Kendrick

(10) Patent No.: US 7,708,019 B2
(45) Date of Patent: May 4, 2010

(54) SPINAL RESTRAINT DEVICE

(75) Inventor: Richard L. Kendrick, Mooresville, NC (US)

(73) Assignee: Kendrick EMS, Inc., Mooresville, NC (US)

( * ) Notice: Subject to any disclaimer, the term of this patent is extended or adjusted under 35 U.S.C. 154(b) by 999 days.

(21) Appl. No.: 11/450,180

(22) Filed: Jun. 9, 2006

(65) Prior Publication Data

US 2007/0287943 A1    Dec. 13, 2007

(51) Int. Cl.
*A61F 5/37*      (2006.01)
*A61F 13/00*     (2006.01)

(52) U.S. Cl. .................. 128/870; 128/846; 128/869; 602/19

(58) Field of Classification Search .............. 128/869, 128/870, 875, 877, 846; 602/19; 5/628; D24/190
See application file for complete search history.

(56) References Cited

U.S. PATENT DOCUMENTS

| 2,309,464 A | 1/1943 | Lucci |
| 2,489,828 A | 11/1949 | Springer |
| 2,753,864 A | 7/1956 | Weidemann, Jr. |
| 3,158,875 A | 12/1964 | Fletcher |
| 3,274,453 A | 9/1966 | Dixon |
| 3,469,268 A | 9/1969 | Phillips |
| 4,143,654 A | 3/1979 | Sherman |
| 4,211,218 A | 7/1980 | Kendrick |
| 5,027,833 A * | 7/1991 | Calkin .................. 128/870 |

* cited by examiner

*Primary Examiner*—Kim M Lewis
(74) *Attorney, Agent, or Firm*—Summa, Additon & Ashe, P.A.

(57) ABSTRACT

A spinal restraint device includes a body member with a head support portion, a neck support portion, and a back support portion. Left and right body wrap portions extend from the back support portion, and left and right head wrap portions extend from the neck support portion, and these portions respectively wrap around an individual's torso and head and are secured to each other to secure the torso and head against movement. A chest flap section is provided in the left and right body wrap portions for folding away from the individual's chest, for comfort or for better access to the chest area. Declaration buckles and straps are also provided for securing the spinal restraint device (and individual) to a support board or stretcher. Other benefits are realized from the positioning of securing straps and leg straps and the dimensions of the body wrap portions.

26 Claims, 1 Drawing Sheet

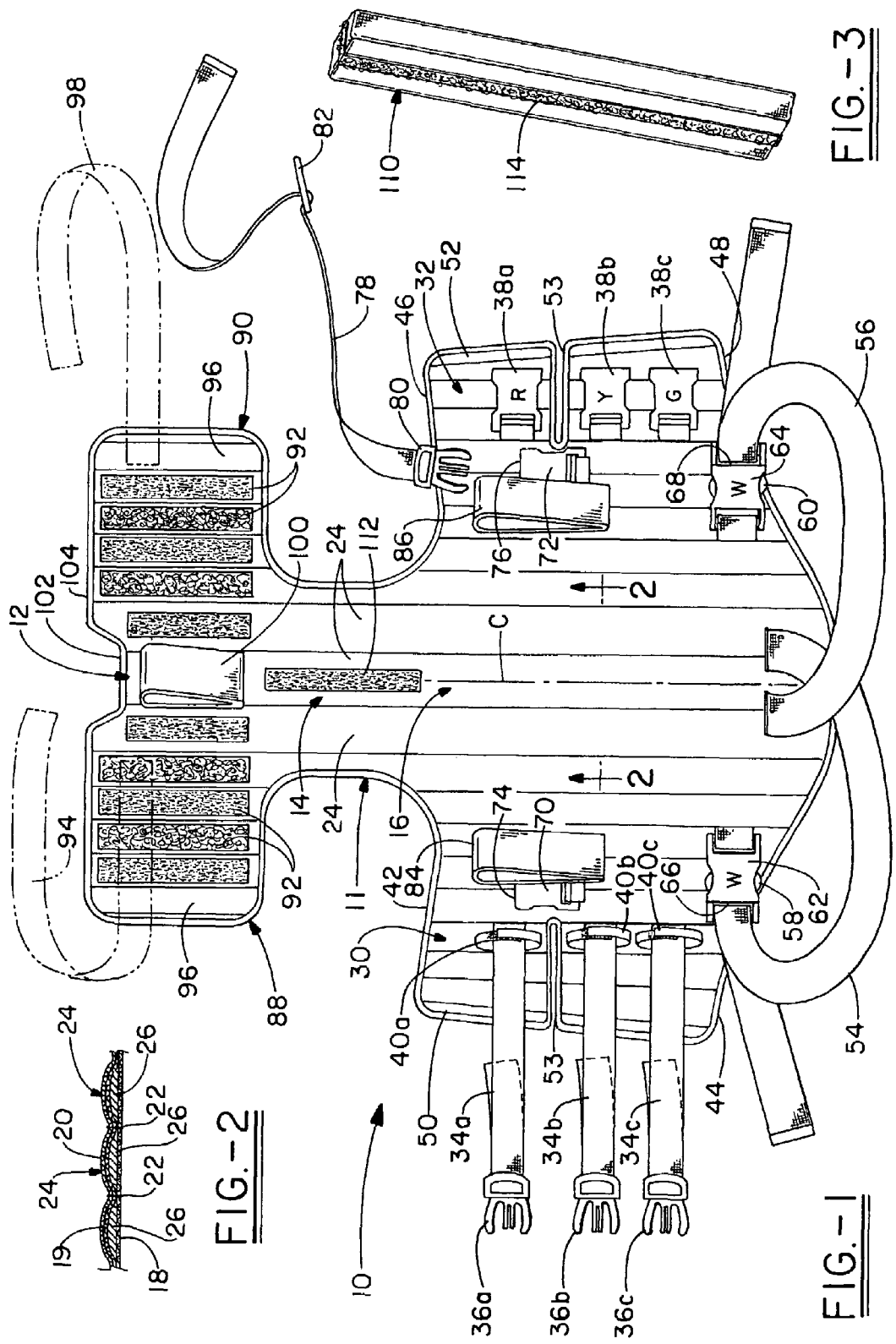

SPINAL RESTRAINT DEVICE

TECHNICAL FIELD

The present invention relates to spinal restraint devices, particularly those constructed and arranged for use with emergency patients. Spinal restraint devices in accordance with this invention are particularly useful in the case of an automobile accident, an injury to a player in an athletic event, a construction site accident, or any other type of an accident in which the injured person may have received a serious injury to his back or neck area.

BACKGROUND ART

Care must be taken when removing and carrying an injured person to a location equipped to administer medical treatment. Moving the injured person requires extreme caution whenever moving the body could cause further injury. Hastily removing an individual from the site of an accident and transporting them to a medical center might cause injuries beyond those suffered in the actual accident. This is particularly true in the case of back and/or neck injuries. Thus, if the patient has had an injury to the spine, it is of the utmost importance to immobilize the body during the handling of the patient. This need is recognized, and, to some extent, all litters and stretchers are designed with an eye toward maintaining the patient in an immobile as well as comfortable position.

The problems associated with moving an injured individual are exacerbated when it is difficult to access the injured individual, as, for example, in the case of a car accident in which the structure of the car has been compromised. The present inventor's prior U.S. Pat. No. 4,211,218 provides a spinal restraint device that has been well received because it provides a device that can be employed in location where injured individual is fairly inaccessible. While this device is well received, certain aspects of its structure make the device difficult to use with certain people and in certain situations, and it has been found that specific structural features of known spinal restraint devices can be altered to improve performance and usefulness. Thus, this invention provides a spinal restraint device improving upon those structures of the prior art.

SUMMARY OF THE INVENTION

It is an object of the invention to provide a spinal restraint device that can easily be slipped beneath the back of an injured victim of an automobile accident that is sitting in a bucket seat.

It is also an object to provide a spinal restraint device that wraps around the torso and head of an injured person thereby giving maximum immobilization of the injured person's head, neck, and back area.

It is another object to provide a spinal restraint device that is very compact in size when not being utilized and which easily and quickly unfolds when the necessity to use it occurs.

It is another object to provide a spinal restraint device which incorporates structure along its back surface for hoisting the injured person vertically out of inaccessible locations.

It is an additional object to provide a spinal restraint device that is economical to manufacture and relatively maintenance free.

It is a further object to provide a spinal restraint device that will provide maximum immobilization of the head, neck, and back of the injured person during his transportation to a medical treatment center.

It is yet another object to provide a spinal restraint device that can be placed on an injured individual in such a way that the chest area is uncovered, for comfort and/or for access to employ defibrillators, monitoring electrodes, stethoscopes, and other medical equipment.

It is another object to provide a spinal restraint device that is specifically adapted to aid in immobilizing and removing an injured individual from a driver's side of a car.

It is another object to provide a spinal restraint device that includes leg straps that are positioned to be more comfortable in use than those of the prior art, and also for facilitating their employment in confined areas, for example, in the interior of a car.

It is still another object to provide a spinal restraint device that can be collapsed to an elongated cylindrical configuration that can be slipped into an elongated carrying bag.

At least one of the forgoing objects will be accomplished by the improvements in spinal restraint devices hereinafter disclosed in particularly preferred embodiments, although it is to be appreciated that the spirit and scope of this invention is not limited by such particular embodiments.

A spinal restraint device including a body member having a head support portion, a neck support portion, and a back support portion; a left-side body wrap portion extending laterally from a left side of said back support portion and including a chest flap section; and a right-side body wrap portion extending laterally from a right side of said back support portion and including a chest flap section, wherein said back support portion is adapted to be placed against an individual's back, said left-side and said right-side body wrap portions are adapted to be passed under the individual's arms to wrap around respective sides of the individual's torso, and said chest flap sections of said left-side and said right-side body wrap portions are adapted to be selectively folded back laterally to prevent said body wrap portions from covering the chest area of the patient.

A spinal restraint device including a body member having a head support portion, a neck support portion, and a back support portion; a left-side body wrap portion extending laterally from a left side of said back support portion and defined longitudinally by a left arm end and a left hip end, said left hip end extending laterally at a greater distance than said left arm end; a right-side body wrap portion extending laterally from a right side of said back support portion and defined longitudinally by a right arm end and a right hip end, said right hip end extending laterally at a greater distance than said right arm end, wherein said back support portion is adapted to be placed against an individual's back, and said left-side and said right-side body wrap portions are adapted to be passed under the individual's arms to wrap around respective sides of the individual's torso; a plurality of body cinching straps extending from one of said left-side body wrap portion and said right-side body wrap portion; and a plurality of fasteners attached to the other of said left-side body wrap portion and said right-side body wrap portion for securing the spinal restraint device around the individual's torso by securing said plurality of body cinching straps to said plurality of fasteners, across said left- and said right-side body wrap portions.

A spinal restraint device including a body member having a head support portion, a neck support portion, and a back support portion; a left-side body wrap portion extending laterally from a left side of said back support portion; a right-side body wrap portion extending laterally from a right side of said back support portion, wherein said back support portion is adapted to be placed against an individual's back, said left-side and said right-side body wrap portions are adapted to be passed under the individual's arms to wrap around respective sides of the individual's torso; and a left-side deceleration strap fastener positioned on said left-side body wrap portion such that, when said left-side body wrap portion is passed under the individual's arm to wrap around the left side of the individual's torso, said left-side deceleration strap fastener points upwardly toward the individual's left shoulder; a right-side deceleration strap fastener positioned on said right-side body wrap portion such that, when said right-side body wrap portion is passed under the individual's arm to wrap around the right side of the individual's torso, said right-side deceleration strap fastener points upwardly toward the individual's right shoulder; and a deceleration strap having opposed ends selectively secured to said left-side and said right-side deceleration strap fastener.

A spinal restraint device including a body member having a head support portion, a neck support portion, and a back support portion; a left-side head wrap portion extending laterally from a left side of said head support portion to a left end; a right-side head wrap portion extending laterally from a right side of said head support portion, wherein said head support portion is adapted to be positioned behind an individual's head and said left-side and said right-side head wrap portions are adapted to be folded around respective sides of the individual's head; hook-and-loop securement means provided on said left-side and said right-side head wrap portions selected from the group consisting of loop fabric for securing hook straps and hook fabric for securing loop straps in a hook-and-loop type fastening; and adhesive strap securement means provided on said left-side and said right-side head wrap portions.

A spinal restraint device on a patient including a body member having a head support portion, a neck support portion, and a back support portion, a left body wrap portion extending laterally from a left side of said back support portion and providing a female left leg fastener; a right body wrap portion extending laterally from a right side of said back support portion and providing a female right leg fastener; a right leg strap secured at one end to said back support portion and providing a male right leg fastener movable along the length of the right leg strap, a left leg strap secured at one end to said back support portion and providing a male left leg fastener movable along the length of the left leg strap, wherein said back support portion is adapted to be placed against an individual's back, said left body wrap portion is adapted to be wrapped around the left side of the individual's torso, with said female left leg fastener positioned on said left body wrap portion such that it rests proximate the individual's hip bone, said right body wrap portion is adapted to be wrapped around the right side of the individual's torso, with said female right leg fastener positioned on said left body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

A spinal restraint device including a body member having a head support portion, a neck support portion, and a back support portion; a left-side body wrap portion extending laterally from a left side of said back support portion and defined longitudinally by a left arm end and a left hip end, said left hip end extending laterally at a greater distance than said left arm end, said left-side body wrap portion including a chest flap section proximate said left arm end and further including a female left leg fastener; a right-side body wrap portion extending laterally from a right side of said back support portion and defined longitudinally by a right arm end and a right hip end, said right hip end extending laterally at a greater distance than said right arm end, said right-side body wrap portion including a chest flap section proximate said right arm end and further including a female right leg fastener, a right leg strap secured at one end to said back support portion and providing a male right leg fastener movable along the length of the right leg strap, a left leg strap secured at one end to said back support portion and providing a male left leg fastener movable along the length of the left leg strap, a left-side head wrap portion extending laterally from a left side of said head support portion to a left end; a right-side head wrap portion extending laterally from a right side of said head support portion, wherein said head support portion is adapted to be positioned behind an individual's head and said left-side and said right-side head wrap portions are adapted to be folded around respective sides of the individual's head; hook-and-loop securement means provided on said left-side and said right-side head wrap portions for securing straps in a hook-and-loop type fastening; and adhesive strap securement means provided on said left-side and said right-side head wrap portions; a plurality of body cinching straps extending from one of said left-side body wrap portion and said right-side body wrap portion; and a plurality of fasteners attached to the other of said left-side body wrap portion and said right-side body wrap portion for securing the spinal restraint device around the individual's torso by securing said plurality of body cinching straps to said plurality of fasteners; a left-side deceleration strap fastener positioned on said left-side body wrap portion such that, when said left-side body wrap portion is passed under the individual's arm to wrap around the left side of the individual's torso, said left-side deceleration strap fastener points upwardly toward the individual's left shoulder; a right-side deceleration strap fastener positioned on said right-side body wrap portion such that, when said right-side body wrap portion is passed under the individual's arm to wrap around the right side of the individual's torso, said right-side deceleration strap fastener points upwardly toward the individual's right shoulder; and a deceleration strap having opposed ends selectively secured to said left-side and said right-side deceleration strap fastener, wherein said back support portion is adapted to be placed against an individual's back, said left-side body wrap portion is adapted to be wrapped around the left side of the individual's torso, with said female left leg fastener positioned on said left body wrap portion such that it rests proximate the individual's hip bone, said right-side body wrap portion is adapted to be wrapped around the right side of the individual's torso, with said female right leg fastener positioned on said right body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion, and said chest flap sections of said left-side and said right-side body wrap portions are adapted to be selectively folded back laterally to prevent said body wrap portions from covering the chest area of the patient.

A preferred exemplary spinal restraint device according to the concepts of the present invention is shown by way of example in the accompanying drawings without attempting to show all the various forms and modifications in which the invention might be embodied, the invention being measured by the appended claims and not by the details of the specification.

BRIEF DESCRIPTION OF THE DRAWINGS

FIG. 1 is a rear plan view illustrating a spinal restraint device in accordance with this invention;

FIG. 2 is a cross section view taken along lines 2-2 of FIG. 1; and

FIG. 3 is a general perspective view of an auxiliary padding that is optionally employed with the spinal restraint device.

PREFERRED EMBODIMENT FOR CARRYING OUT THE INVENTION

With reference to FIG. 1, it can be seen that a particularly preferred spinal restraint device of this invention is shown and designated by the numeral 10. Spinal restraint device 10 includes a body member 11 having a head support portion 12, a neck support portion 14, and a back support portion 16. The embodiment shown herein includes all of the improvements made to prior art spinal restraint devices (e.g., U.S. Pat. No. 4,211,218), but it will be appreciated that one or more of these improvements might be practiced within the scope of lesser preferred embodiments that are contemplated by this invention.

From the cross section of FIG. 2, it can be seen that the body member 11 has a front sheet-like layer 18 of flexible material, a middle sheet-like layer 19 of flexible material, and a rear sheet-like layer 20 of flexible material. Laterally spaced longitudinal rows of stitching 22 secure these front, middle, and rear sheet-like layers of flexible material together. The stitching 22 extends substantially across the entire height of the body member 11 and forms a plurality of longitudinal sleeves 24. Stiffener members 26 can be and are preferably located within longitudinal sleeves 24. They are preferably made of high density polyethylene so that they provide increased strength to place the device behind the patient and yet comfortable enough to conform and contour to the patient's body shape, providing good contact and patient support. The front sheet-like layer 18 is placed against the injured individual's back during use, with the various elements on the rear sheet-like layer 20 being employed to secure the spinal restraint device 10 to the individual and to help transport the individual thus secured. This configuration also allows the spinal restraint device to be collapsed to an elongated cylindrical configuration that can be slipped into an elongated carrying bag.

A left body wrap portion 30 extends laterally from the left side of back support portion 16, and a right body wrap portion 32 extends laterally from the right side of back support portion 16. A plurality of body cinching straps, designated by 34a, 34b, and 34c, are secured to the left body wrap portion 30, each providing a male torso fastener 36a, 36b, and 36c, respectively. A plurality of female torso fasteners, designated by 38a, 38b, and 38c, are secured to the right body wrap portion 32, and serve to receive the male torso fasteners 36a, 36b and 36c, respectively. It can be seen that each one of the female torso fasteners is secured at a substantially identical longitudinal position on the body member 11 as is a corresponding body cinching strap, and, therefore, each of the plurality of body cinching straps 34a-c may be extended straight across an injured patient's stomach and chest area to be secured to an aligned female torso fastener 38a-c. The rear surface of left body wrap portion 30 preferably includes a plurality of packing loops 40a-c into which an appropriate body cinching strap 34a-c may be stored when the spinal restraint device is not in use. These packing loops are mating velcro straps, but need not be limited thereto as other means for storing the length of the body cinching straps may be employed.

The left body wrap portion 30 is defined longitudinally by a left arm end 42 and a left hip end 44, with the left hip end 44 extending laterally a greater distance than does the left arm end 42 such that, laterally, the left body wrap portion 30 gradually gets wider as you move from the left arm end 42 to the left hip end 44. Likewise, the right body wrap portion 32 is defined longitudinally by a right arm end 46 and a right hip end 48, with the right hip end 48 extending laterally a greater distance than does the right arm end 46, such that, laterally, the right body wrap portion 32 gradually gets wider as you move from the right arm end 46 to the right hip end 48. The left body wrap portion 30 includes a left chest flap section 50, and the right body wrap portion 32 includes a right chest flap section 52. These chest flap sections 50 and 52 can be folded back from the remainder of their respective body wrap portions 30 and 32, because they are separated longitudinally therefrom, as at slits 53. The body cinching strap 34a, the male torso fastener 36a and the packing loop 40a are secured to the left chest flap section 50, and the female torso fastener 38a is secured to the right chest flap section 52.

A left leg strap 54 and a right leg strap 56 are secured to the back support portion 16, and are provided with a male left leg fastener 58 and a male right leg fastener 60, respectively. The male leg fasteners 58 and 60 are movable along the length of their respective strap. The male left leg fastener 58 is provided to mate with the female left leg fastener 62 on the left body wrap portion 30, and the male right leg fastener 60 is provided to mate with the female right leg fastener 64. In accordance with a preferred configuration, the left leg strap 54 is secured to the back support portion 16 on the right-hand side of centerline C of the back support portion 16, and the right leg strap 56 is secured to the back support portion 16 on the left-hand side of centerline C. It will be appreciated that, in use, the centerline C is placed to align with the patient's spine, and, thus, in use, the left leg strap 54 extends from a position just to the right side of the patient's spine, between the patient's legs, across the front of the patient's left leg, and then connects to the female left leg fastener 62. Similarly, the right leg strap 56 extends from a position just to the left side of the patient's spine, between the patient's legs, across the front of the patient's right leg, and then connects to the female left leg fastener 62. The female left leg fastener 62 and the female right leg fastener 64 extend laterally and provide open ends 66 and 68, which respectively accept the insertion of the male left leg fastener 58 and the male right leg fastener 60. The female left leg fastener 62 and the female right leg fastener 64 are positioned on left body wrap portion 30 such that they rest proximate the patient's hip bone when spinal restraint device 10 is placed on a patient. In the prior art, the leg fasteners on the body wrap portion extend diagonally, that is, both laterally and longitudinally, and are positioned much higher in relation to the patient's hip bone when the prior art devices are worn. The new configuration taught here, with straps extending from opposite sides of a spine centerline and connecting to laterally extending fasteners placed lower than in the prior art to be proximate the hip bone, is more comfortable for the patient, because the strap extends across a lower part of the leg and more contact is between the strap and the leg so as to spread the pressure of the strap over a larger area.

A left deceleration strap fastener 70 is secured to the left body wrap portion 30, and a right deceleration strap fastener 72 is secured to the right body wrap portion 32. These fasteners 70 and 72 preferably extend longitudinally, with their respective open ends 74 and 76 pointing upwardly, and are provided to receive a deceleration strap such as that shown in FIG. 1 as a separate strap element designated by the numeral 78. The deceleration strap 78 includes a fixed male fastener 80 and a movable male fastener 82, and these male fasteners 80 and 82 can selectively be secured at either the left deceleration strap fastener 70 or the right deceleration strap fastener 72, both of which are female fasteners in this preferred embodiment. Movable male fastener 82 is secured to strap 78 so as to be movable along its length if strap 78 is manipulated to pass through fastener 82, but fastener 82 also retains its position along strap 78 absent such manipulation. This is much like the common means for adjusting back pack straps and the like. Left and right lifting loops 84 and 86 are provided on the left body wrap portion 30 and the right body wrap portion 32, respectively.

A left head wrap portion 88 extends laterally from the left side of the head support portion 12, and a right head wrap portion 90 extends laterally from the right side thereof. The rear surfaces of left and right head wrap portions 88 and 90 each include a plurality of laterally spaced longitudinally extending hook-and-loop securement means 92, that interact with securing straps 94 (FIG. 1) in a hook-and-loop type fastening. In this preferred embodiment, the hook-and-loop securement means 92 is selected to be either loop fabric, for interacting with securing straps providing hooks, or hook fabric, for interacting with securing straps providing loops. As is known, securing straps 94 are typically secured around the forehead and chin.

Notably, the prior art shows a plurality of securement means extending in close proximity to the distal ends of left and right head wrap portions of a spinal restraint device. Hook-and-loop type fastening is employed to secure the head wrap portions around the patient's head. Unfortunately, it has been found that the hook-and-loop type fastening does not perform well in certain situations, particularly, if the hook or loop fabric or both are wet or dirty or have debris already stuck to them (lint, pieces of string, etc.). Thus, alternative securement means are provided in the present invention, as at the adhesive strap securement means 96 on left and right head wrap portions 88 and 90. The adhesive strap securement means 96 are provided as smooth fabric segments that will interact with one or more adhesive straps 98, as opposed to the hook or loop type securing strap(s) 94 that are to interact under appropriate conditions with hook-and-loop securement means 92.

A lifting loop 100 is provided on the head support portion 12, preferably along centerline C. A notch 102 is provided at top edge 104 of the head support portion 12.

To use the spinal restraint device 10, the front side (providing front sheet-like layer 18) is placed against a patient's back, with the centerline C aligned as best as possible with the patient's spine. The left and the right body wrap portions 30 and 32 are passed under the patient's left and right arms, respectively, and are wrapped around respective sides of the patient's torso. These body wrap portions are then secured around the patient's body by securing one or more of the body cinching straps 36*a-c* to its respective fastener 38*a-c*. Notably, because the left and right bodywrap portions extend further laterally near the hips than near the arms, the force of the lowest strap is distributed more evenly than in configurations wherein the body wrap portions extend laterally to the same extent at the top and bottom. If necessary to pull the patient's shoulders backward toward the device 10, the deceleration strap 78 can be used. The strap 78 is first placed behind the patient's shoulders proximate the area of fastening strip 112, and is passed over the patient's shoulders to wrap over the shoulders and connect to deceleration strap fasteners 70 (at one end) and 72 (at the other end). The deceleration strap 78 is then pulled to shorten it and thus pull the patient's shoulders back toward the spinal restraint device 10.

The head wrap portions 88 and 90 are secured around a patient's head by the use of hook-an-loop type straps and/or adhesive-type straps (such as adhesive straps 98). Notably, notch 102 gives a rescuer easier access to the back of the patient's head for the placement of any padding that may be required for stabilizing the head.

The left and right leg straps 54 and 56 are secured around the appropriate leg, as already described. Thus secured, the patient is beneficially immobilized to a great degree, and can be moved by the use of left and right lifting loops 84 and 86 and the head area lifting loop 100. If placed on his or her back on a stretcher or other support board, the patient wearing the spinal restraint device 10 can be secured thereto by the use of deceleration strap 78, by securing the deceleration strap 78 to one of the left or right deceleration strap fasteners 70 or 72, passing the deceleration strap around the patient's back, around the support board, and securing the other end of the deceleration strap to the other of the left or right deceleration strap fastener 70 or 72. Auxiliary padding such as that designated by the numeral 110 in FIG. 3 may be secured to the rear surface (at rear sheet-like layer 20) of the spinal restraint device 10. In the embodiment shown, hook-and-loop fastening strip 112 is provided along centerline C at the rear surface of spinal restraint device 10, and this strip 112 interacts with a hook-and-loop strip 114 on auxiliary padding 110 to allow one to place padding along the patient's spine.

Advantageously, the left and right chest flap sections 50 and 52 may be selectively placed either against the patient's chest or folded back laterally to prevent the body wrap portions from covering the chest area of the patient. This allows a paramedic or other individual treating the patient to selectively access the chest (for example, for a defibrillator) or provide additional bodywrapping support, as desired. For female patients, the chest flap sections can be folded back for comfort, particularly for patients with larger busts.

Because the left hip end 44 of the left body wrap portion 30 extends a greater lateral distance than does the left arm end 42, and, likewise, the right hip end 48 of right body wrap portion 32 extends a greater lateral distance than does the right arm end 46, the spinal restraint device 10 of this invention is more conducive to use on larger individuals, particularly with larger stomachs/waists. Again, this contributes to comfort, while not compromising support.

By designing spinal restraint device 10 with body cinching straps 34*a*, 34*b* and 34*c* extending from left body wrap portion 40, device 10 is especially adapted for use in immobilizing and removing an injured individual from the left hand side (in most countries, the driver's side) of a vehicle. More particularly, when used, spinal restraint device 10 can be slipped behind an injured person sitting on the left hand side of a vehicle, and straps 34*a*, 34*b*, 34*c* will extend out toward and/or through the left side door, where the rescuer is located. Thus, the rescuer will not have to lean over the injured person to proceed to secure spinal restraint device 10.

In light of the forgoing, it should be apparent that the present invention provides improvements in the art of spinal restraint devices, and one or more of the objects of the invention are achieved by the improvements disclosed. This invention, however, is not to be limited in scope to the specific embodiments disclosed in accordance with patent law requirements, inasmuch as, also in accordance with the patent laws, this invention is to be defined by the claims herein.

What is claimed is:

1. A spinal restraint device comprising:
   a body member having a head support portion, a neck support portion, and a back support portion;
   a left-side body wrap portion extending laterally from a left side of said back support portion and including a chest flap section;
   a right-side body wrap portion extending laterally from a right side of said back support portion and including a chest flap section, wherein said back support portion is adapted to be placed against an individual's back, said left-side and said right-side body wrap portions are adapted to be passed under the individual's arms to wrap around respective sides of the individual's torso, and said chest flap sections of said left-side and said right-side body wrap portions are adapted to be selectively folded back laterally to prevent said body wrap portions from covering the chest area of the patient;
   a left-side deceleration strap fastener positioned on said left-side body wrap portion such that, when said left-side body wrap portion is passed under the individual's arm to wrap around the left side of the individual's torso, said left-side deceleration strap fastener points upwardly toward the individual's left shoulder;
   a right-side deceleration strap fastener positioned on said right-side body wrap portion such that, when said right-side body wrap portion is passed under the individual's arm to wrap around the right side of the individual's torso, said right-side deceleration strap fastener points upwardly toward the individual's right shoulder; and
   a deceleration strap having opposed ends selectively secured to said left-side and said right-side deceleration strap fastener.

2. The spinal restraint device of claim 1, wherein said left-side body wrap portion is defined longitudinally by a left arm end and a left hip end, said left hip end extending laterally at a greater distance than said left arm end;
   said right-side bodywrap portion is defined longitudinally by a right arm end and a right hip end, said right hip end extending laterally at a greater distance than said right arm end; and the spinal restraint device further comprises:
      a plurality of body cinching straps extending from one of said left-side body wrap portion and said right-side body wrap portion;
      and a plurality of fasteners attached to the other of said left-side body wrap portion and said right-side body wrap portion for securing the spinal restraint device around the individual's torso by securing said plurality of body cinching straps to said plurality of fasteners, across said left- and said right-side body wrap portions.

3. The spinal restraint device of claim 2, further comprising:
   a left-side deceleration strap fastener positioned on said left-side body wrap portion such that, when said left-side body wrap portion is passed under the individual's arm to wrap around the left side of the individual's torso, said left-side deceleration strap fastener points upwardly toward the individual's left shoulder;
   a right-side deceleration strap fastener positioned on said right-side body wrap portion such that, when said right-side body wrap portion is passed under the individual's arm to wrap around the right side of the individual's torso, said right-side deceleration strap fastener points upwardly toward the individual's right shoulder; and
   a deceleration strap having opposed ends selectively secured to said left-side and said right-side deceleration strap fastener.

4. The spinal restraint device of claim 3, further comprising:
   a left-side head wrap portion extending laterally from a left side of said head support portion to a left end;
   a right-side head wrap portion extending laterally from a right side of said head support portion, wherein said head support portion is adapted to be positioned behind an individual's head and said left-side and said right-side head wrap portions are adapted to be folded around respective sides of the individual's head;
   hook-and-loop securement means provided on said left-side and said right-side head wrap portions selected from the group consisting of loop fabric for securing hook straps and hook fabric for securing loop straps in a hook-and-loop type fastening; and
   adhesive strap securement means provided on said left-side and said right-side head wrap portions.

5. The spinal restraint device of claim 3, wherein said left-side body wrap portion provides a female left leg fastener, and said right-side body wrap portion provides a female right leg fastener, the spinal restraint further comprising:
   a right leg strap secured at one end to said back support portion and providing a male right leg fastener movable along the length of the right leg strap,
   a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side body wrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

6. The spinal restraint device of claim 2, further comprising:
   a left-side head wrap portion extending laterally from a left side of said head support portion to a left end;
   a right-side head wrap portion extending laterally from a right side of said head support portion, wherein said head support portion is adapted to be positioned behind an individual's head and said left-side and said right-side head wrap portions are adapted to be folded around respective sides of the individual's head;
   hook-and-loop securement means provided on said left-side and said right-side head wrap portions selected from the group consisting of loop fabric for securing hook straps and hook fabric for securing loop straps in a hook-and-loop type fastening; and adhesive strap securement means provided on said left-side and said right-side head wrap portions.

7. The spinal restraint device of claim 6, wherein said left-side body wrap portion provides a female left leg fastener, and said right-side body wrap portion provides a female right leg fastener, the spinal restraint further comprising:

a right leg strap secured at one end to said back support portion and providing a male right leg fastener movable along the length of the right leg strap, a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side body wrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

8. The spinal restraint device of claim 2, wherein said left-side body wrap portion provides a female left leg fastener, and said right-side body wrap portion provides a female right leg fastener, the spinal restraint further comprising:

a right leg strap secured at one end to said back support portion and providing a male right leg fastener movable along the length of the right leg strap, a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side body wrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

9. The spinal restraint device of claim 1, further comprising:

a left-side head wrap portion extending laterally from a left side of said head support portion to a left end;

a right-side head wrap portion extending laterally from a right side of said head support portion, wherein said head support portion is adapted to be positioned behind an individual's head and said left-side and said right-side head wrap portions are adapted to be folded around respective sides of the individual's head;

hook-and-loop securement means provided on said left-side and said right-side head wrap portions selected from the group consisting of loop fabric for securing hook straps and hook fabric for securing loop straps in a hook-and-loop type fastening; and adhesive strap securement means provided on said left-side and said right-side head wrap portions.

10. The spinal restraint device of claim 9, wherein said left-side body wrap portion provides a female left leg fastener, and said right-side body wrap portion provides a female right leg fastener, the spinal restraint further comprising:

a right leg strap secured at one end to said back support portion and providing a male right leg fastener movable along the length of the right leg strap, a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side body wrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

11. The spinal restraint device of claim 1, wherein said left-side body wrap portion provides a female left leg fastener, and said right-side body wrap portion provides a female right leg fastener, the spinal restraint further comprising:

a right leg strap secured at one end to said back support portion and providing a male right leg fastener movable along the length of the right leg strap, a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side body wrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

12. The spinal restraint device of claim 1, further comprising:

a left-side head wrap portion extending laterally from a left side of said head support portion to a left end;

a right-side head wrap portion extending laterally from a right side of said head support portion, wherein said head support portion is adapted to be positioned behind an individual's head and said left-side and said right-side head wrap portions are adapted to be folded around respective sides of the individual's head;

hook-and-loop securement means provided on said left-side and said right-side head wrap portions selected from the group consisting of loop fabric for securing hook straps and hook fabric for securing loop straps in a hook-and-loop type fastening; and adhesive strap securement means provided on said left-side and said right-side head wrap portions.

13. The spinal restraint device of claim 12, wherein said left-side body wrap portion provides a female left leg fastener, and said right-side body wrap portion provides a female right leg fastener, the spinal restraint further comprising:

a right leg strap secured at one end to said back support portion and providing a male right leg fastener movable along the length of the right leg strap, a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side body wrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

14. The spinal restraint device of claim 1, wherein said left-side body wrap portion provides a female left leg fastener, and said right-side body wrap portion provides a female right leg fastener, the spinal restraint further comprising:

a right leg strap secured at one end to said back support portion and providing a male right leg fastener movable along the length of the right leg strap, a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side body wrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right side body wrap portion.

15. A spinal restraint device comprising:

a body member having a head support portion, a neck support portion, and a back support portion;

a left-side body wrap portion extending laterally from a left side of said back support portion and defined longitudinally by a left arm end and a left hip end, said left hip end extending laterally at a greater distance than said left arm end;

a right-side body wrap portion extending laterally from a right side of said back support portion and defined longitudinally by a right arm end and a right hip end, said right hip end extending laterally at a greater distance than said right arm end, wherein said back support portion is adapted to be placed against an individual's back, and said left-side and said right-side body wrap portions are adapted to be passed under the individual's arms to wrap around respective sides of the individual's torso;

a plurality of body cinching straps extending from one of said left-side body wrap portion and said right-side body wrap portion;

a plurality of fasteners attached to the other of said left-side body wrap portion and said right-side body wrap portion for securing the spinal restraint device around the individual's torso by securing said plurality of body cinching straps to said plurality of fasteners, across said left- and said right-side body wrap portions;

a left-side deceleration strap fastener positioned on said left-side body wrap portion such that, when said left-side body wrap portion is passed under the individual's arm to wrap around the left side of the individual's torso, said left-side deceleration strap fastener points upwardly toward the individual's left shoulder;

a right-side deceleration strap fastener positioned on said right-side body wrap portion such that, when said right-side body wrap portion is passed under the individual's arm to wrap around the right side of the individual's torso, said right-side deceleration strap fastener points upwardly toward the individual's right shoulder; and a deceleration strap having opposed ends selectively secured to said left-side and said right-side deceleration strap fastener.

16. The spinal restraint device of claim 15, further comprising:

a left-side head wrap portion extending laterally from a left side of said head support portion to a left end;

a right-side head wrap portion extending laterally from a right side of said head support portion, wherein said head support portion is adapted to be positioned behind an individual's head and said left-side and said right-side head wrap portions are adapted to be folded around respective sides of the individual's head;

hook-and-loop securement means provided on said left-side and said right-side head wrap portions selected from the group consisting of loop fabric for securing hook straps and hook fabric for securing loop straps in a hook-and-loop type fastening; and adhesive strap securement means provided on said left-side and said right-side head wrap portions.

17. The spinal restraint device of claim 16, wherein said left-side body wrap portion provides a female left leg fastener, and said right-side body wrap portion provides a female right leg fastener, the spinal restraint further comprising:

a right leg strap secured at one end to said back support portion and providing a male right leg fastener movable along the length of the right leg strap, a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side bodywrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

18. The spinal restraint device of claim 15, wherein said left-side body wrap portion provides a female left leg fastener, and said right-side body wrap portion provides a female right leg fastener, the spinal restraint further comprising:

a right leg strap secured at one end to said back support portion and providing a male right leg fastener movable along the length of the right leg strap, a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side body wrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

19. The spinal restraint device of claim 15, further comprising:

a left-side head wrap portion extending laterally from a left side of said head support portion to a left end;

a right-side head wrap portion extending laterally from a right side of said head support portion, wherein said head support portion is adapted to be positioned behind an individual's head and said left-side and said right-side head wrap portions are adapted to be folded around respective sides of the individual's head;

hook-and-loop securement means provided on said left-side and said right-side head wrap portions selected from the group consisting of loop fabric for securing hook straps and hook fabric for securing loop straps in a hook-and-loop type fastening; and adhesive strap securement means provided on said left-side and said right-side head wrap portions.

20. The spinal restraint device of claim 19, wherein said left-side body wrap portion provides a female left leg fastener, and said right-side body wrap portion provides a female right leg fastener, the spinal restraint further comprising:

a right leg strap secured at one end to said back support portion and providing a male right leg fastener movable along the length of the right leg strap, a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side body wrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

21. The spinal restraint device of claim 15, wherein said left-side body wrap portion provides a female left leg fastener, and said right-side body wrap portion provides a female right leg fastener, the spinal restraint further comprising:

a right leg strap secured at one end to said back support portion and providing a male right leg fastener movable along the length of the right leg strap, a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side body wrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

22. A spinal restraint device comprising:

a body member having a head support portion, a neck support portion, and a back support portion;

a left-side body wrap portion extending laterally from a left side of said back support portion;

a right-side body wrap portion extending laterally from a right side of said back support portion, wherein said back support portion is adapted to be placed against an individual's back, said left-side and said right-side body wrap portions are adapted to be passed under the individual's arms to wrap around respective sides of the individual's torso; and a left-side deceleration strap fastener positioned on said left-side body wrap portion such that, when said left-side body wrap portion is passed under the individual's arm to wrap around the left side of the individual's torso, said left-side deceleration strap fastener points upwardly toward the individual's left shoulder;

a right-side deceleration strap fastener positioned on said right-side body wrap portion such that, when said right-side body wrap portion is passed under the individual's arm to wrap around the right side of the individual's torso, said right-side deceleration strap fastener points upwardly toward the individual's right shoulder; and a deceleration strap having opposed ends selectively secured to said left-side and said right-side deceleration strap fastener.

23. The spinal restraint device of claim 22, further comprising:

a left-side head wrap portion extending laterally from a left side of said head support portion to a left end;

a right-side head wrap portion extending laterally from a right side of said head support portion, wherein said head support portion is adapted to be positioned behind an individual's head and said left-side and said right-side head wrap portions are adapted to be folded around respective sides of the individual's head;

hook-and-loop securement means provided on said left-side and said right-side head wrap portions selected from the group consisting of loop fabric for securing hook straps and hook fabric for securing loop straps in a hook-and-loop type fastening; and adhesive strap securement means provided on said left-side and said right-side head wrap portions.

24. The spinal restraint device of claim 23, wherein said left-side body wrap portion provides a female left leg fastener, and said right-side body wrap portion provides a female right leg fastener, the spinal restraint further comprising:

a right leg strap secured at one end to said back support portion and providing a male right leg fastener movable along the length of the right leg strap, a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side body wrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

25. The spinal restraint device of claim 22, wherein said left-side body wrap portion provides a female left leg fastener, and said right-side body wrap portion provides a female right leg fastener, the spinal restraint further comprising:

a right leg strap secured at one end to said back support portion and providing a male right leg fastener movable along the length of the right leg strap, a left leg strap secured at one end to said back support portion and providing a male left leg fastener movable along the length of the left leg strap, wherein said left-side body wrap portion is adapted to be wrapped around the left side of the individual's torso, with said female left leg fastener positioned on said left-side body wrap portion such that it rests proximate the individual's hip bone, said right-side body wrap portion is adapted to be wrapped around the right side of the individual's torso, with said female right leg fastener positioned on said right-side body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion.

26. A spinal restraint device comprising:

a body member having a head support portion, a neck support portion, and a back support portion;

a left-side body wrap portion extending laterally from a left side of said back support portion and defined longitudinally by a left arm end and a left hip end, said left hip end extending laterally at a greater distance than said left arm end, said left-side body wrap portion including a chest flap section proximate said left arm end and further including a female left leg fastener;

a right-side body wrap portion extending laterally from a right side of said back support portion and defined longitudinally by a right arm end and a right hip end, said right hip end extending laterally at a greater distance than said right arm end, said right-side body wrap portion including a chest flap section proximate said right arm end and further including a female right leg fastener, a right leg strap secured at one end to said back support portion and providing a male right leg fastener movable along the length of the right leg strap, a left leg strap secured at one end to said back support portion and providing a male left leg fastener movable along the length of the left leg strap, a left-side head wrap portion extending laterally from a left side of said head support portion to a left end;

a right-side head wrap portion extending laterally from a right side of said head support portion, wherein said head support portion is adapted to be positioned behind an individual's head and said left-side and said right-side head wrap portions are adapted to be folded around respective sides of the individual's head;

hook-and-loop securement means provided on said left-side and said right-side head wrap portions for securing straps in a hook-and-loop fastening; and adhesive strap securement means provided on said left-side and said right-side head wrap portions;

a plurality of body cinching straps extending from one of said left-side body wrap portion and said right-side body wrap portion; and a plurality of fasteners attached to the other of said left-side body wrap portion and said right-side body wrap portion for securing the spinal restraint device around the individual's torso by securing said plurality of body cinching straps to said plurality of fasteners;
a left-side deceleration strap fastener positioned on said left-side body wrap portion such that, when said left-side body wrap portion is passed under the individual's arm to wrap around the left side of the individual's torso, said left-side deceleration strap fastener points upwardly toward the individual's left shoulder;
a right-side deceleration strap fastener positioned on said right-side body wrap portion such that, when said right-side body wrap portion is passed under the individual's arm to wrap around the right side of the individual's torso, said right-side deceleration strap fastener points upwardly toward the individual's right shoulder; and
a deceleration strap having opposed ends selectively secured to said left-side and said right-side deceleration strap fastener, wherein said back support portion is adapted to be placed against an individual's back, said left-side body wrap portion is adapted to be wrapped around the left side of the individual's torso, with said female left leg fastener positioned on said left body wrap portion such that it rests proximate the individual's hip bone, said right-side body wrap portion is adapted to be wrapped around the right side of the individual's torso, with said female right leg fastener positioned on said right body wrap portion such that it rests proximate the individual's hip bone, said left leg strap is adapted to be wrapped around the individual's left leg by passing it over the front of the individual's left thigh and securing said male left leg fastener on said left leg strap to said female left leg fastener on said left body wrap portion, and said right leg strap is adapted to be wrapped around the individual's right leg by passing it over the front of the individual's right thigh and securing said male right leg fastener on said right leg strap to said female right leg fastener on said right body wrap portion, and said chest flap sections of said left-side and said right-side body wrap portions are adapted to be selectively folded back laterally to prevent said body wrap portions from covering the chest area of the patient.

* * * * *